(12) United States Patent
Norton (10) Patent No.: US 9,345,494 B2
(45) Date of Patent: May 24, 2016

(54) ORTHOPAEDIC TOOL HANDLE AND METHOD OF MANUFACTURING SAME

(71) Applicant: Biomet Manufacturing, LLC, Warsaw, IN (US)

(72) Inventor: Daniel R. Norton, Winona Lake, IN (US)

(73) Assignee: Biomet Manufacturing, LLC., Warsaw, IN (US)

( * ) Notice: Subject to any disclaimer, the term of this patent is extended or adjusted under 35 U.S.C. 154(b) by 115 days.

(21) Appl. No.: 13/750,593

(22) Filed: Jan. 25, 2013

(65) Prior Publication Data

US 2014/0214100 A1 Jul. 31, 2014

(51) Int. Cl.
*A61B 17/88* (2006.01)
*A61B 17/17* (2006.01)
*A61B 17/00* (2006.01)

(52) U.S. Cl.
CPC ....... *A61B 17/17* (2013.01); *A61B 2017/00424* (2013.01); *Y10T 29/49* (2015.01)

(58) Field of Classification Search
CPC ............. B25G 1/102; A61B 5/150259; A61B 2017/00424
USPC ................................................ 16/430; 81/489
See application file for complete search history.

(56) References Cited

U.S. PATENT DOCUMENTS

| 4,964,192 A | * | 10/1990 | Marui .............................. 16/421 |
| 6,261,141 B1 | * | 7/2001 | Heap ...................... B63H 16/04 440/101 |
| 8,277,458 B2 | | 10/2012 | Schneider |
| 8,562,647 B2 | | 10/2013 | Kaiser et al. |

* cited by examiner

*Primary Examiner* — David Bates
*Assistant Examiner* — Olivia C Chang
(74) *Attorney, Agent, or Firm* — Schwegman Lundberg & Woessner, P.A.

(57) ABSTRACT

An orthopedic tool includes a handle having an exterior profile defined by a first three-dimensional shape having an exterior surface of revolution about a first axis of rotation, and a second three-dimensional shape having an exterior surface of revolution about a second axis of rotation. The second axis of rotation is offset from the first axis of rotation, whereby the first three-dimensional shape and the second three-dimensional shape intersect to define a volume of intersection. The exterior profile is defined only by the volume of intersection. A shaft extends from the handle.

18 Claims, 8 Drawing Sheets

ORTHOPAEDIC TOOL HANDLE AND METHOD OF MANUFACTURING SAME

BACKGROUND OF THE INVENTION

1. Field of the Invention

The present invention relates to orthopaedic tool handles, and, more particularly, to ergonomically designed orthopaedic tool handles.

2. Description of the Related Art

Suture anchors are resorbable repair devices used to attach soft tissue (e.g., tendons or ligaments) to bone. A suture anchor may be implanted into a predrilled hole formed in a bone, and sutures extend from the suture anchor to attach or anchor the soft tissue to the bone. A drill guide may be used to form the hole in the bone. A drill bit is inserted through a central bore in the drill guide, and forms the hole at a specified depth in cortical bone. The drill bit is removed and a suture anchor is inserted through the central bore in the drill guide and seated within the preformed hole in the bone. The drill guide is then removed, leaving the suture anchor and suture in place for attaching the soft tissue to the bone.

An example of such a suture anchor is the JuggerKnot™ suture anchor, which is disclosed in U.S. patent application Ser. No. 12/915,962 and incorporated herein by reference.

A drill guide used with a suture anchor is adequate for the purpose of forming the hole in the bone and seating the suture anchor within the preformed hole. Such a drill guide typically includes a handle with a common shape, such as a cylindrical shape, teardrop shape, etc. Depending upon the size and shape of the surgeon's hand, as well as the angle at which the surgeon grasps the handle, the handle may or may not feel comfortable within the surgeon's hand.

SUMMARY OF THE INVENTION

The present invention provides a handle for an orthopaedic tool, which is created by overlaying two three-dimensional shapes, and retaining the volume of intersection between the two shapes.

The invention in one form is directed to an orthopaedic tool, including a handle having an exterior profile defined by a first three-dimensional shape having an exterior surface of revolution about a first axis of rotation, and a second three-dimensional shape having an exterior surface of revolution about a second axis of rotation. The second axis of rotation is offset from the first axis of rotation, whereby the first three-dimensional shape and the second three-dimensional shape intersect to define a volume of intersection. The exterior profile is defined only by the volume of intersection. A shaft extends from the handle.

The invention in another form is directed to a handle for a tool, including an exterior profile defined by a first three-dimensional shape having an exterior surface of revolution about a first axis of rotation, and a second three-dimensional shape having an exterior surface of revolution about a second axis of rotation, said second axis of rotation being offset from said first axis of rotation, whereby said first three-dimensional shape and said second three-dimensional shape intersect to define a volume of intersection, said exterior profile being defined only by said volume of intersection.

The invention in yet another form is directed to a method of manufacturing a handle for an orthopaedic tool, including the steps of:

generating a three-dimensional model of the handle, comprising the sub-steps of:

forming a first three-dimensional shape having an exterior surface of revolution about a first axis of rotation;

forming a second three-dimensional shape having an exterior surface of revolution about a second axis of rotation;

overlaying the second three-dimensional shape onto the first three-dimensional shape, with the second axis of rotation being offset from the first axis of rotation; and creating the three-dimensional model using only a volume of intersection between the first three-dimensional shape and the second three-dimensional shape; and using the three-dimensional model in a manufacturing process to create the handle for an orthopaedic tool.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate embodiments of the invention, and such exemplifications are not to be construed as limiting the scope of the invention in any manner.

DETAILED DESCRIPTION OF THE INVENTION

Referring now to the drawings, and more particularly to FIGS. 1-6, there is shown a tool in the form of an orthopaedic tool 20. In the illustrated embodiment, orthopaedic tool 20 is configured as a drill guide, but may be configured as a different type of orthopaedic tool, depending upon the application. Another embodiment of a drill guide 22 is illustrated in FIG. 7, which has an exterior shape similar to that of drill guide 20 shown in FIGS. 1-6 (the primary difference being that drill guide 22 has slots in the exterior surface of the handle).

Drill guide 20 generally includes a handle 24 and shaft 26. Shaft 26 may also be referred to as a cannula when part of an orthopaedic tool, but for other applications may be simply referred to as a shaft. Handle 24 may be constructed from any suitable material, such as plastic, etc.

Handle 24 has an exterior profile 28 with a three-dimensional shape which provides a more ergonomic and thus comfortable feel for a user, regardless of the size of the hand of the user, or the relative angle of alignment between the handle and the hand of the user. The exterior profile 28 of handle 24 is generated using two different three-dimensional shapes which are overlayed relative to each other, described in more detail below.

Figure 8:
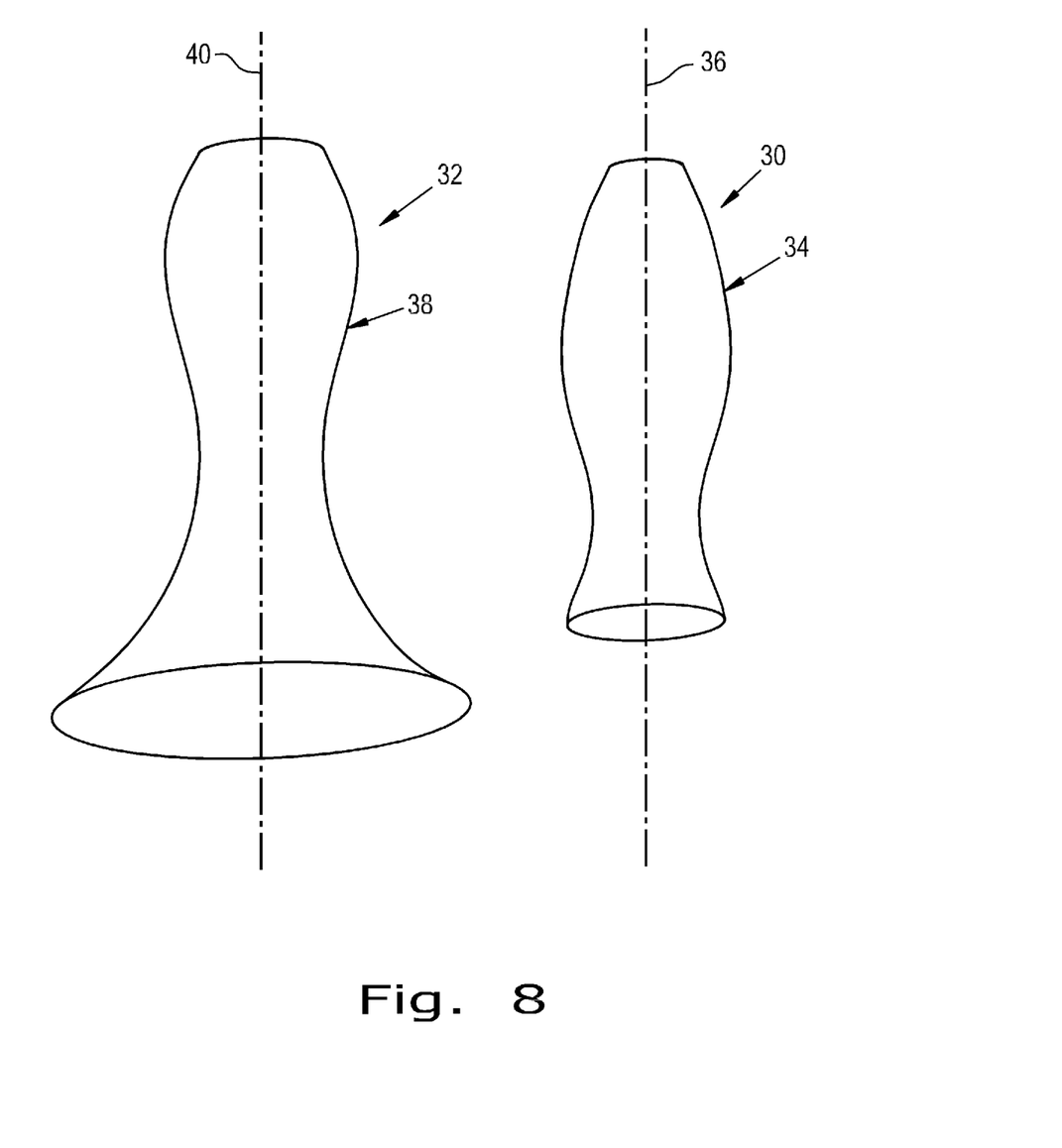
FIG. 8 is a perspective view showing two exemplary three-dimensional shapes used to create the handle shown in FIGS. 1-6.
Figure 9:
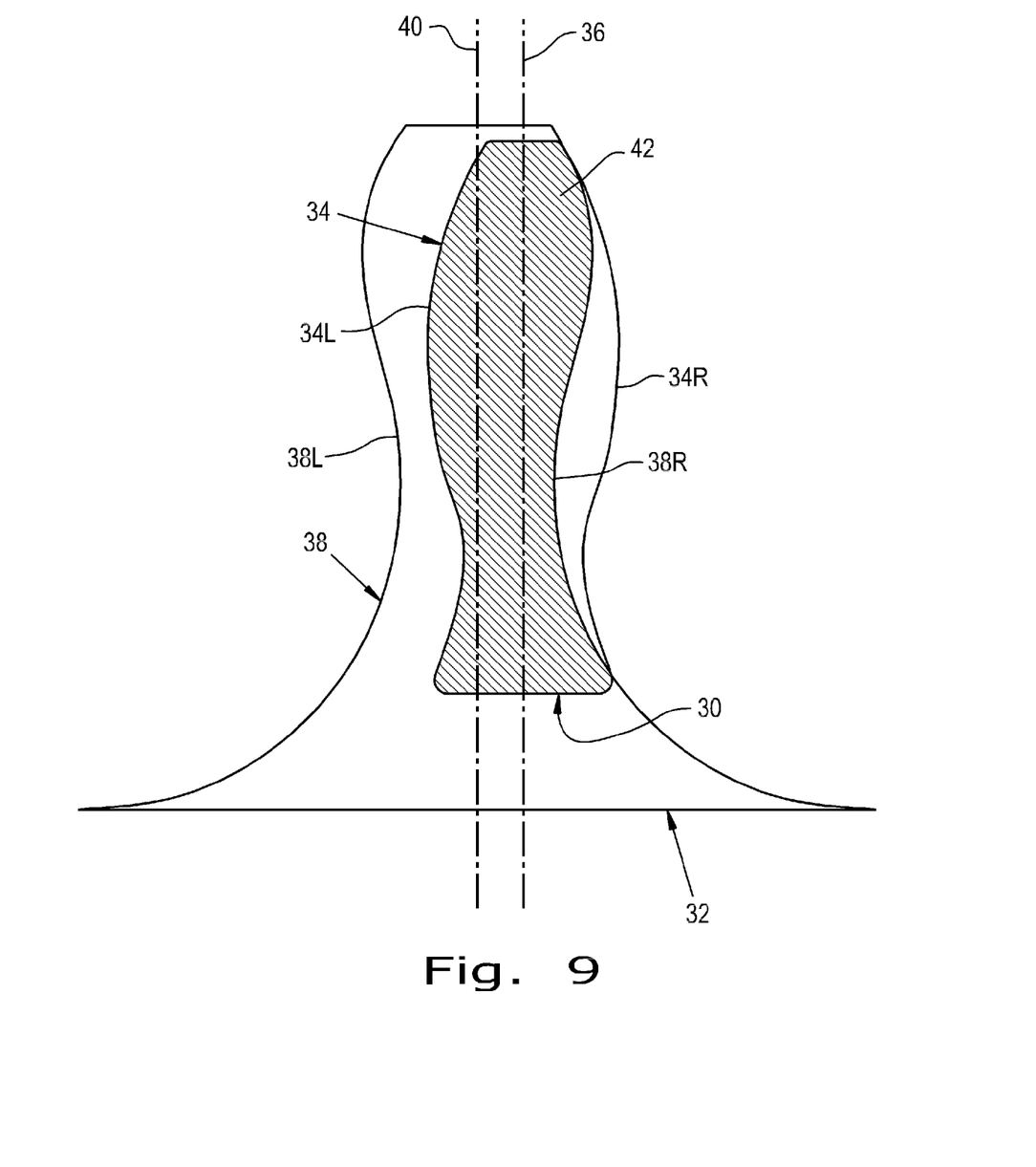
FIG. 9 is a side view showing the larger three-dimensional shape overlaid on the smaller three-dimensional shape.
Figure 10:
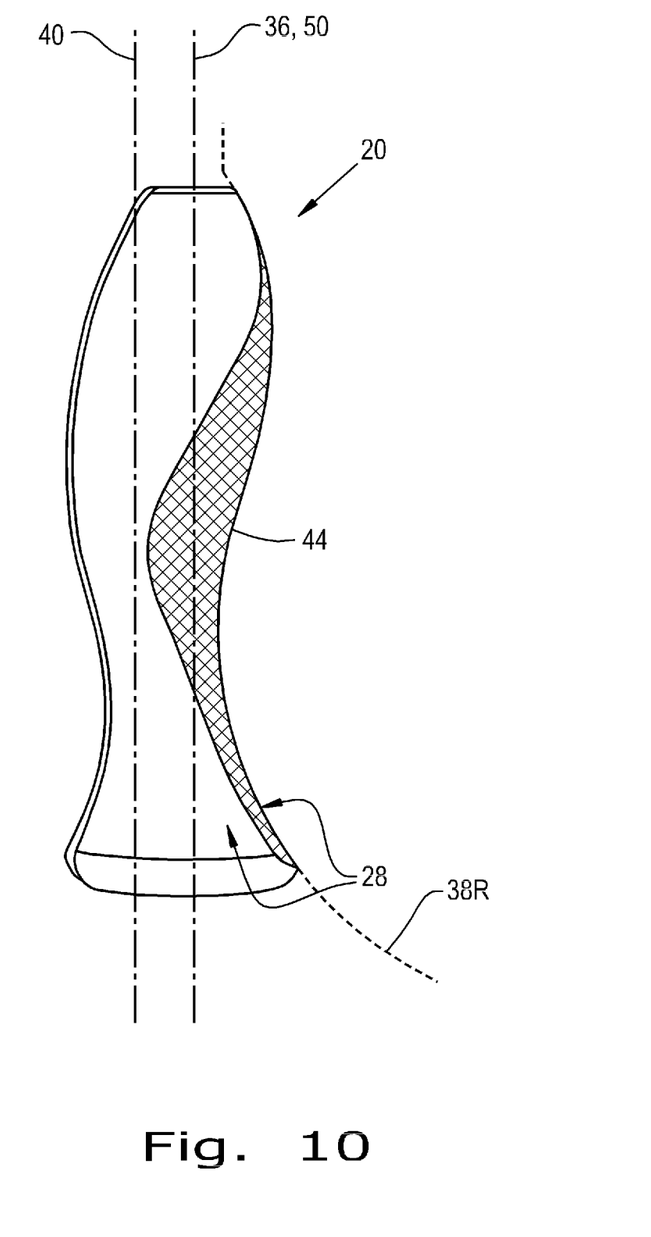
FIG. 10 is a perspective view showing the surface of intersection on the smaller three-dimensional shape, defining the final handle exterior profile.

Referring now to FIGS. 8-10, conjunctively, exterior profile 28 is defined by a first three-dimensional shape 30 and a second three-dimensional shape 32. First three-dimensional shape 30 has an exterior surface of revolution 34 about a first axis of rotation 36. Likewise, second three-dimensional shape 32 has an exterior surface of revolution 38 about a second axis of rotation 40. In the illustrated embodiment, first three-dimensional shape 30 is generally torpedo shaped, and second three-dimensional shape 32 is generally bell shaped. However, first and second three-dimensional shapes 30, 32 may have any desired size and shape, depending upon the specific application.

Handle 24 is constructed by overlaying first and second three-dimensional shapes 30, 32 on top of each other, and retaining the resultant volume of intersection therebetween. More particularly, referring to FIG. 9, second three-dimensional shape 32 is overlaid on first three-dimensional shape 30 such that first and second axes of rotation 36, 40 are offset relative to each other and pass through each of first and second three-dimensional shapes 30, 32. For ease of reference, the left (L) and right (R) of the exterior surfaces of revolution 34, 38 are shown in FIG. 9, and labeled 34L, 34R, 38L and 38R, respectively. The overlapping volume of intersection 42 shown with crosshatch lines in FIG. 9 is the portion that is retained to define exterior profile 28 of handle 24. Thus, as viewed in FIG. 9, the left side 34L of the exterior surface of revolution 34 defines the left side of handle 24, and the right side 38R of the exterior surface of revolution 38 defines the right side of handle 24. The remaining portion of each of first three-dimensional shape 30 and second three-dimensional shape 32 that is not crosshatched in FIG. 9 is trimmed (deleted) from the final shape of handle 24.

FIG. 10 illustrates the final shape of handle 24, with the surface of intersection 44 forming a portion of the exterior profile 28 of handle 24. Surface of intersection 44 corresponds to the portion of exterior surface of revolution 38 that is rotated through first three-dimensional shape 30 (i.e., the right side 38R shown in FIG. 9).

Figure 1:
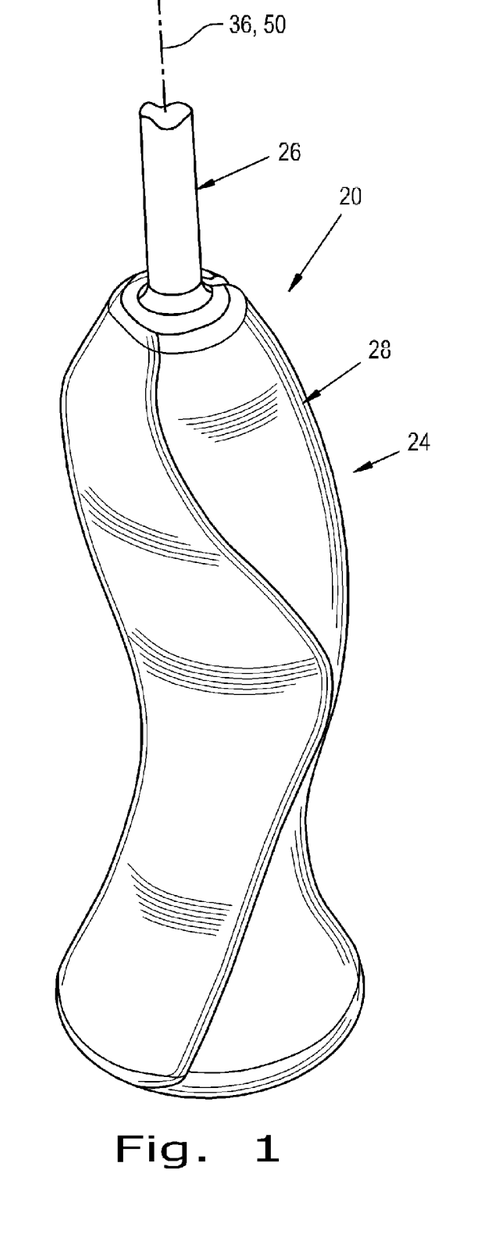
FIG. 1 is a perspective view of an embodiment of an orthopaedic tool handle of the present invention.
Figure 2:
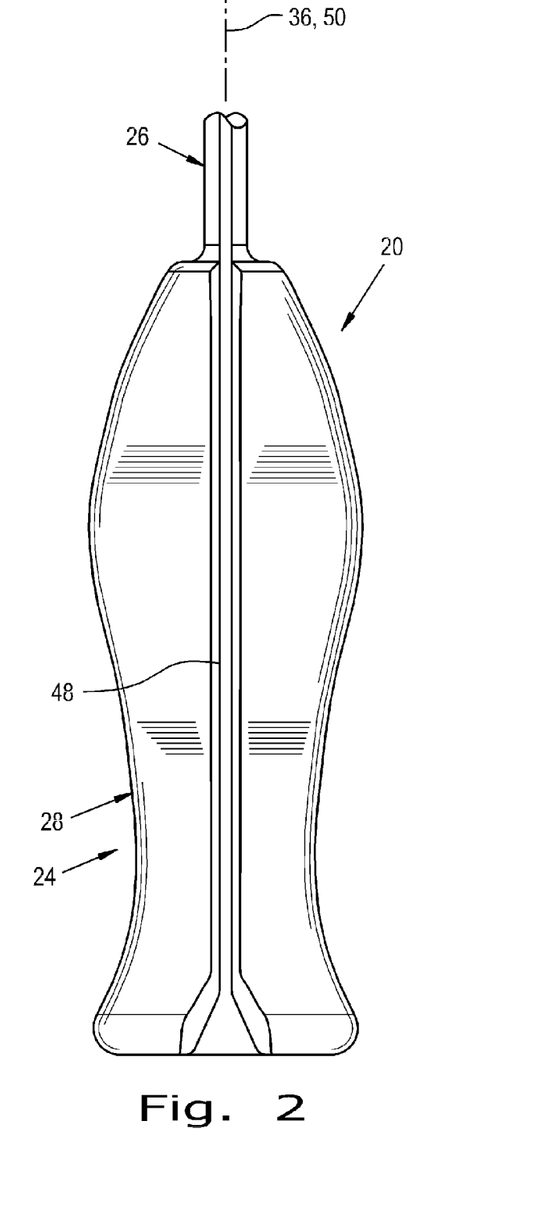
FIG. 2 is a side view of the orthopaedic tool handle shown in FIG. 1.
Figure 3:
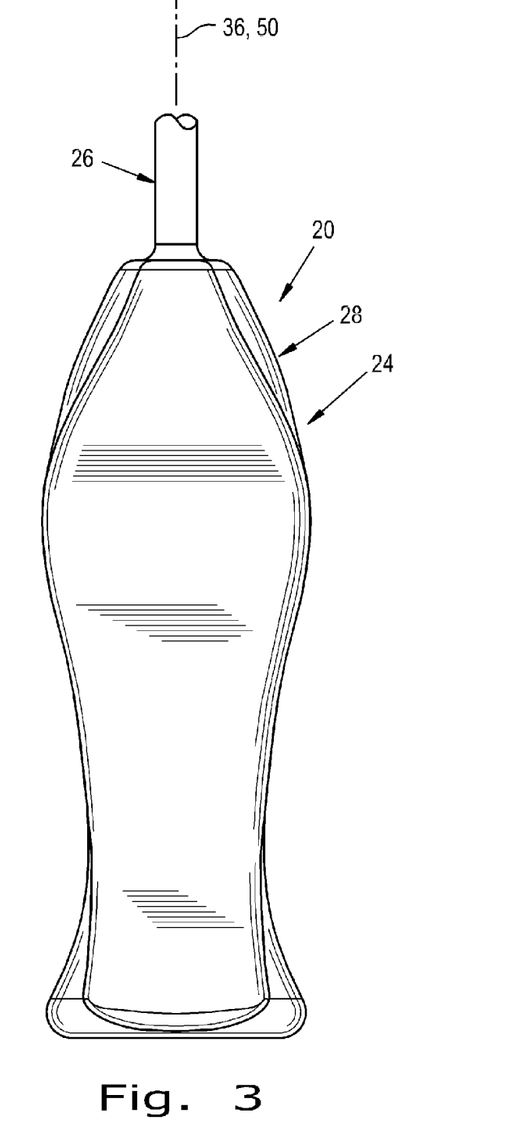
FIG. 3 is another side view of the orthopaedic tool handle shown in FIGS. 1 and 2.
Figure 4:
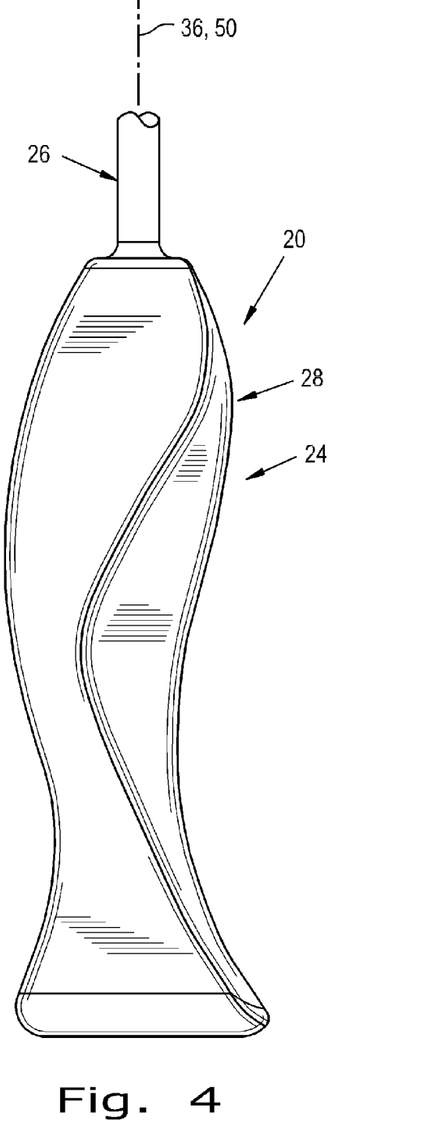
FIG. 4 is another side view of the orthopaedic tool handle shown in FIGS. 1-3.
Figure 5:
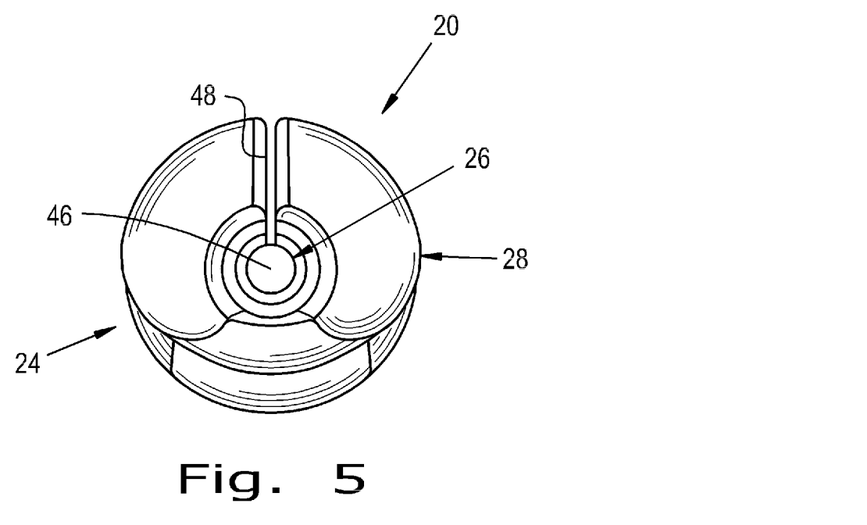
FIG. 5 is an end view of the orthopaedic tool handle shown in FIGS. 1-4.
Figure 6:
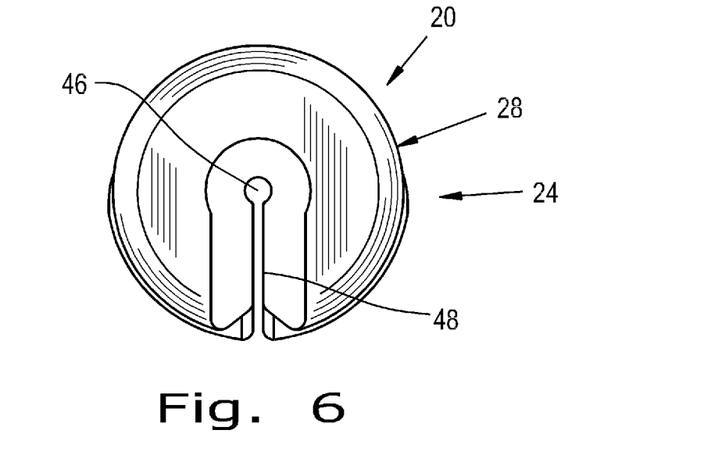
FIG. 6 is an opposite end view of the orthopaedic tool handle shown in FIGS. 1-5.
Figure 7:
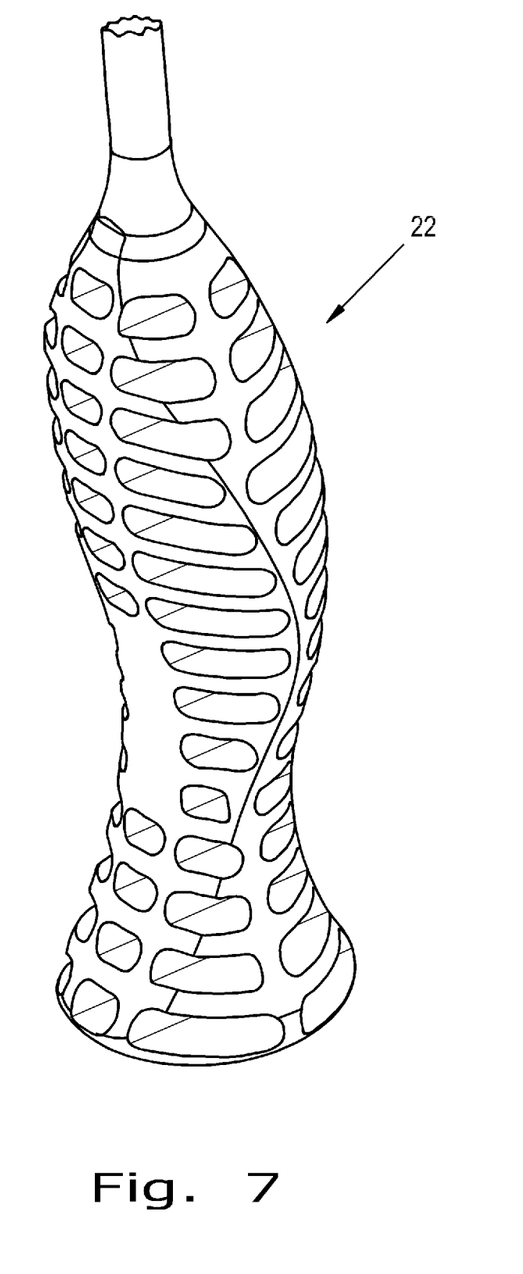
FIG. 7 is a perspective view of another embodiment of an orthopaedic tool handle of the present invention.

When the orthopaedic tool is configured as a drill guide 20 as described above, handle 24 and shaft 26 may each optionally include a central bore 46 allowing a drill bit (not shown) to pass therethrough for forming a hole in a bone (FIGS. 5 and 6). Moreover, handle 24 may optionally include a longitudinally extending slot 48 in communication with central bore 46 (FIGS. 2, 5 and 6). Slot 48 allows suture from a suture anchor (not shown) to be removed laterally therethrough after the suture anchor is implanted within the preformed hole in the bone.

Moreover, in the embodiment illustrated above, first axis of rotation 36 and second axis of rotation 40 are positioned parallel to each other, and first axis of rotation 36 is also positioned generally coincident with a longitudinal axis 50 of shaft 26 (FIGS. 1-4 and 10). However, first axis of rotation 36 and second axis of rotation 40 may be positioned offset but at any desired relative angle therebetween, i.e., parallel or skewed. Moreover, longitudinal axis 50 of shaft 26 need not necessarily be positioned coincident with first axis of rotation 36. For example, longitudinal axis 50 may be positioned at an acute angle relative to first axis of rotation 36.

Figure 11:
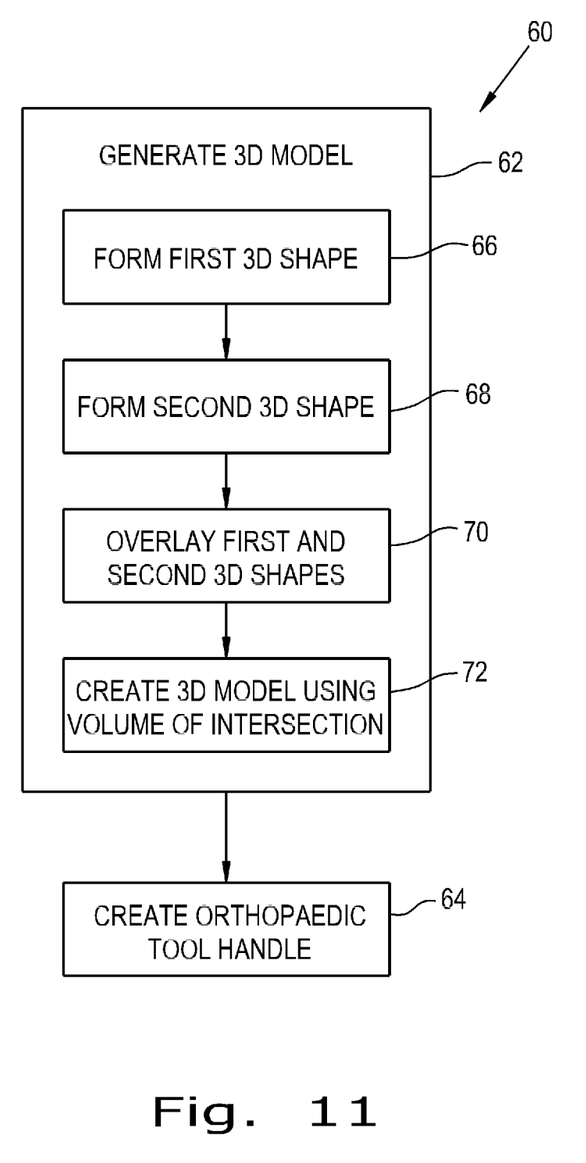
FIG. 11 is a flowchart showing an embodiment of the method of the present invention for manufacturing a handle for an orthopaedic tool.

Referring now to FIG. 11, there is shown a flowchart of an embodiment of a method 60 of the present invention for manufacturing a handle 24 of an orthopaedic tool 20. In general, method 60 includes the broad steps of generating a three-dimensional model of handle 24 (block 62), and using the three-dimensional model in a manufacturing process to create a handle 24 of orthopaedic tool/drill guide 20 (block 64).

To generate the three-dimensional model of handle 24 (block 62), a first three-dimensional shape 30 and a second three-dimensional shape 32 are each formed with a desired exterior surface of revolution 34, 38 and corresponding axis of rotation 36, 40 (blocks 66 and 68). Second three-dimensional shape 32 is overlaid onto first three-dimensional shape 30, with second axis of rotation 40 being offset from first axis of rotation 36 (block 70). After being overlaid, first three-dimensional shape 30 and second three-dimensional shape 32 intersect to define a volume of intersection 42 and a surface of intersection 44, with a portion of first three-dimensional shape 30 lying outside of second three-dimensional shape 32. The three-dimensional model is created using only the volume of intersection 42 (block 72). One way of doing this is to delete/remove the portion of first three-dimensional shape 30 that lies outside of second three-dimensional shape 32, adjacent surface of intersection 44. In addition, second three-dimensional shape 32 is removed from first three-dimensional shape 30, such that only a non-deleted portion of first three-dimensional shape 30 remains to define the three-dimensional model (corresponding to volume of intersection 42).

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A handle for a tool, comprising:
   an exterior profile extending along a longitudinal direction, the exterior profile defined by:
   a first three-dimensional shape having a first exterior surface of revolution about only a first axis of rotation, and a second three-dimensional shape having a second exterior surface of revolution about only a second axis of rotation,
   said second axis of rotation being offset from said first axis of rotation,
   said first and second exterior surfaces of revolution each having a concave portion, a convex portion, and an inflection point between the concave portion and the convex portion,
   said inflection point of the second exterior surface of revolution being longitudinally offset from said inflection point of the first exterior surface of revolution,
   whereby said first three-dimensional shape and said second three-dimensional shape intersect to define a volume of intersection, said exterior profile being defined only by said volume of intersection.

2. The handle of claim 1, wherein said first three-dimensional shape and said second three-dimensional shape intersect to define a surface of intersection, and a portion of said first three-dimensional shape lies within said second three-dimensional shape, said exterior profile only including said surface of intersection and said portion of said first three-dimensional shape that lies within said second three-dimensional shape.

3. The handle of claim 1, wherein said exterior profile of said handle includes a portion of said first three-dimensional shape, bounded in part by said surface of intersection.

4. The handle of claim 1, wherein said first axis of rotation is positioned one of parallel and skewed relative to said second axis of rotation.

5. The handle of claim 4, wherein said first axis of rotation and said second axis of rotation are generally parallel to each other and pass through each of said first three-dimensional shape and said second three-dimensional shape.

6. The handle of claim 1, wherein said first three-dimensional shape is generally torpedo shaped.

7. The handle of claim 1, wherein said handle includes a central bore and a longitudinally extending slot in communication with said central bore.

8. An orthopaedic tool, comprising:
   a handle extending along a longitudinal direction, the handle having an exterior profile defined by:
      a first three-dimensional shape having a first exterior surface of revolution about only a first axis of rotation, said first exterior surface of revolution having first concave portion, a first convex portion, and a first inflection point between the first concave portion and the first convex portion, and
      a second three-dimensional shape having a second exterior surface of revolution about only a second axis of rotation, said second axis of rotation being offset from said first axis of rotation, said second exterior surface of revolution having a second concave portion, a second convex portion, and a second inflection point between the second concave portion and the second convex portion,
      said second inflection point being longitudinally offset from said first inflection point,
      whereby said first three-dimensional shape and said second three-dimensional shape intersect to define a volume of intersection,
      said exterior profile being defined only by said volume of intersection; and
   a shaft extending from said handle.

9. The orthopaedic tool of claim 8, wherein said first three-dimensional shape and said second three-dimensional shape intersect to define a surface of intersection, and a portion of said first three-dimensional shape lies within said second three-dimensional shape, said exterior profile only including said surface of intersection and said portion of said first three-dimensional shape that lies within said second three-dimensional shape.

10. The orthopaedic tool of claim 8, wherein said exterior profile of said handle includes a portion of said first three-dimensional shape, bounded in part by said surface of intersection.

11. The orthopaedic tool of claim 8, wherein said shaft extends from an end of said handle and has a longitudinal axis, and said first axis of rotation is generally coincident with said longitudinal axis.

12. The orthopaedic tool of claim 8, wherein said first axis of rotation is positioned one of parallel and skewed relative to said second axis of rotation.

13. The orthopaedic tool of claim 12, wherein said first axis of rotation and said second axis of rotation are generally parallel to each other and pass through each of said first three-dimensional shape and said second three-dimensional shape.

14. The orthopaedic tool of claim 8, wherein said first three-dimensional shape is generally torpedo shaped.

15. The orthopaedic tool of claim 8, wherein said orthopaedic tool is a drill guide.

16. The orthopaedic tool of claim 15, wherein said handle includes a central bore and a longitudinally extending slot in communication with said central bore.

17. A handle for a tool, the handle comprising:
   an exterior profile defined by:
      a first three-dimensional shape having an exterior surface of revolution about only a first axis of rotation, and
      a second three-dimensional shape having an exterior surface of revolution about only a second axis of rotation,
      said second axis of rotation being skewed relative to said first axis of rotation,
      whereby said first three-dimensional shape and said second three-dimensional shape intersect to define a volume of intersection,
      said exterior profile being defined only by said volume of intersection.

18. The handle of claim 17, wherein said first three-dimensional shape and said second three-dimensional shape intersect to define a surface of intersection, and a portion of said first three-dimensional shape lies within said second three-dimensional shape, said exterior profile only including said surface of intersection and said portion of said first three-dimensional shape that lies within said second three-dimensional shape.

* * * * *